United States Patent [19]

Taniyama et al.

[11] 4,150,068
[45] Apr. 17, 1979

[54] FLAME RETARDANT FOR SYNTHETIC RESINS

[75] Inventors: Susumu Taniyama, Toyonaka; Masami Taniguchi, Takatsuki, both of Japan

[73] Assignee: Mitsubishi Gas Chemical Company, Inc., Tokyo, Japan

[21] Appl. No.: 892,026

[22] Filed: Mar. 31, 1978

Related U.S. Application Data

[63] Continuation of Ser. No. 708,297, Jul. 26, 1976, abandoned.

[30] Foreign Application Priority Data

Jul. 24, 1975 [JP] Japan ................................. 50-90548

[51] Int. Cl.² ........................... C07F 9/14; C08K 5/49
[52] U.S. Cl. ............................... 260/930; 260/953; 260/974; 260/45.75 D
[58] Field of Search ................ 260/930, 974, 953, 978

[56] References Cited

U.S. PATENT DOCUMENTS

| | | | |
|---|---|---|---|
| 2,058,394 | 10/1936 | Arvin | 260/930 X |
| 3,163,670 | 12/1964 | Rosenmund et al. | 260/930 |
| 3,761,543 | 9/1973 | Gunsher | 260/930 X |

Primary Examiner—Anton H. Sutto
Attorney, Agent, or Firm—Flynn & Frishauf

[57] ABSTRACT

Flame retardant for synthetic resins comprising an oligomer having the following structural formula:

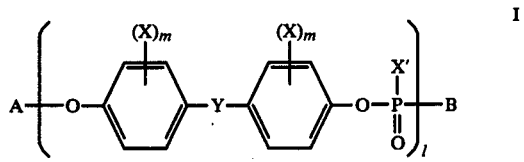

wherein Y is

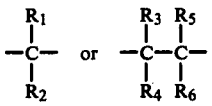

wherein $R_1$, $R_2$, $R_3$, $R_4$, $R_5$ and $R_6$ are independently H or alkyl of $C_1$–$C_3$, X and X' are independently Br or Cl, A is H or a residue of a terminator selected from the group consisting of phenol, alkylphenol, halo-nucleus-substituted phenol, halo-nucleus-substituted alkylphenol, aniline or halo-nucleus-substituted aniline, B is OH or said residue, m is 1 or 2, and l is integer of from 1 to 10.

10 Claims, No Drawings

FLAME RETARDANT FOR SYNTHETIC RESINS

This is a continuation of application Ser. No. 708,297, filed July 26, 1976, now abandoned.

BACKGROUND OF THE INVENTION

This invention relates to a flame retardant for synthetic resins, and particularly relates to a flame retardant for synthetic resins comprising an oligomer having repeated units of

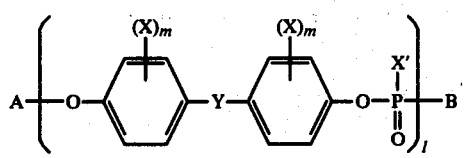

The flame retardant for synthetic resins of the present invention is stable to heat, does not substantially impair the properties of the synthetic resins and has flame retardance effect.

Generally, articles made from synthetic resin are flammable. A variety of flame retardants for synthetic resins, such as organic halides, and organic phosphorus compounds have been proposed in the prior art. However, some of the flame retardants of the prior art are unstable to heat. Some of the flame retardants which are stable to heat tend to discolor the articles made from synthetic resins incorporating the flame retardant and to lower the physical properties, such as the mechanical strength of said articles.

A variety of flame retardants have been developed in order to overcome the disadvantages of the flame retardants composed of the organic halide compounds. For example, in Japanese Public Disclosure No. 49-131234 (laid open), a compound having the formula

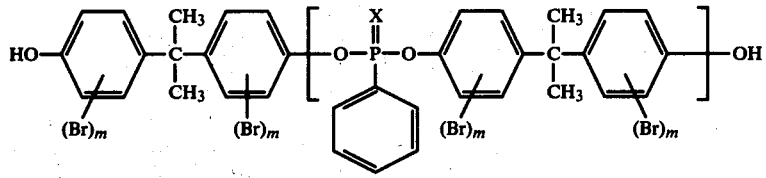

wherein X is O or S, m is integer of from 2 to 4 and l is integer of from 1 to 50 disclosed as a flame retardant for a synthetic resin. In Japanese Patent Publication No. 47-44537, the compound having the formula

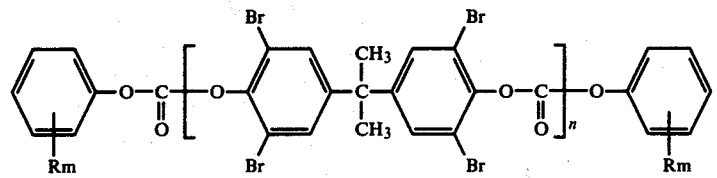

wherein R is H or lower alkyl, m is integer of from 1 to 5 and n is integer of from 2 to 10 is disclosed as a flame retardant for a synthetic resin.

However, when these flame retardants are added to a polyester or polycarbonate which has flame retardance property per se they enhance said flame retardance effect. However, when they are added to polystyrene, high-impact polystyrene or ABS resin which is flammable, they give little or no flame retardant property to the resin.

We have carried out experiments on flame retardancy of the compounds disclosed in Japanese Public Disclosure No. 49-131234 (laid open). In high-impact polystyrene (sold under the trade name of "Styrone 492" by Asahi Dow Co.) were incorporated 20% by weight of such a compound and 5% by weight of antimony trioxide based on the total weight of high-impact polystyrene, the flame retardant and antimony trioxide. A molded article was formed from the resulting mixture. The flame retardancy of the article was tested in accordance with UL 94 test method (Standard for Flammability Tests of Plastic Materials for Parts in Devices and Appliance UL 94, Sept. 1973). The class of the retardancy was 94 v-2. That is the drippings of the resin were observed to fall. This shows that the flame retardancy of the compound was not sufficient.

We have have also carried out an experiment on the flame retardancy of an oligomer of tetrabromobisphenol A polycarbonate disclosed in Japanese Public Disclosure No. 47-44537. In polystyrene (sold under the trade name of "Styrone 666" by Asahi Dow Co.) were incorporated 20% by weight of said oligomer and 5% by weight of antimony trioxide based on the total weight of the polystyrene, flame retardant and antimony trioxide. A molded article was formed from the resulting mixture. The flame retardancy of the article was tested in accordance with Ul 94 Standard. The class of the flame retardancy was 94 v-2. This shows that the flame retardancy of this compound, too, is not sufficient. In the above two experiments the class of UL 94 v-2 in the test of UL 94 Standard shows that drippings of the resin fall on cotton cloth, thereby burning the cloth. This shows there is possibility of causing secondary ignition. Therefore, it was apparent from the above two experiments that the flame retardants as disclosed in Disclosure No. 49-131234 and Publication No. 47-44537 impart poor flame retardancy to high-impact polystyrene and polystyrene when incorporated therein. Consequently, there is need for a flame retardant for synthetic resins having such fire-retardancy effect that in case a resin containing the fire retardant burns, drippings of the resin do not fall.

Also, a tetrabromobisphenol A oligomer terminated with a halo-substituted phenol is disclosed in U.S. Pat. No. 3,846,469 as a flame retardant. However, it was found from our flaming-test that this oligomer had the same flame retardancy as that of an oligomer disclosed in Japanese Patent Publication No. 47-44537.

SUMMARY OF THE INVENTION

One object of this invention is to provide a fire retardant for synthetic resins which gives an excellent fire retardancy effect when incorporated in a flammable resin.

Another object of this invention is to provide a flame retardant which, when incorporated in synthetic resins, does not substantially impair the properties of the synthetic resins.

DETAILED DESCRIPTION OF THE INVENTION

The present invetion relates to a flame retardant for synthetic resins comprising an oligomer having the following structural formula:

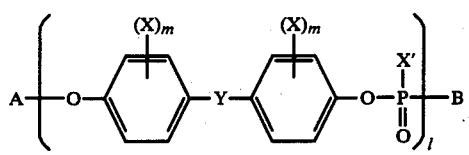

wherein Y is

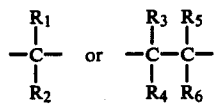

wherein $R_1$, $R_2$, $R_3$, $R_4$, $R_5$ and $R_6$ independently H or alkyl of $C_1$–$C_3$; $X_1$ and $X'$ are independently Br or Cl; A is H or a residue of a terminator selected from the group consisting of phenol; alkylphenol, such as p-tert-butylphenol; halonucleus-substituted phenol, such as di- or tri-bromophenol; halo-nucleus-substituted alkylphenol, such as 2,6-dibromo-p-tert-butylphenol; aniline or halonucleus-substituted aniline, such as di- or tri-bromoaniline; B is OH or said residue; m is 1 or 2; and l is integer of from 1 to 10. Such terminators are well known in the art.

It is preferred that a flame retardant for synthetic resins comprises an oligomer having the following structural formula

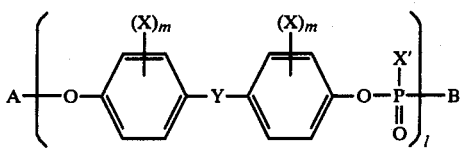

wherein Y is

X is Br or Cl, X' is Cl, A is H and B is OH, m is 1 or 2 and l is integer of from 1 to 10.

The oligomer represented by the formula I is prepared by dehydrohalogenation reaction of a phosphorus oxyhalide having the formula II $$POX_3'$$ II wherein X' is Cl or Br, with the halogenated dihydroxy compound having the formula III

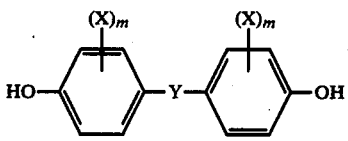

wherein Y is

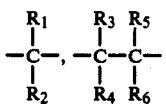

wherein $R_1$, $R_2$, $R_3$, $R_4$, $R_5$ and $R_6$ are independently H or alkyl of $C_1$–$C_3$ X is Cl or Br, and m is 1 or 2. The above reaction may be effected by a conventional solvent method. That is, the halogenated dihydroxy compound represented by Formula III and a material, such as sodium hydroxide, may be dissolved in a solvent, such as, for example, methylene chloride, chlorobenzene, pyridine, toluene and xylene. A solution of the phosphorus oxyhalide represented by formula II in methylene chloride is suitably added dropwise to the solution of the halogenated dihydroxy compound over a time interval of from about 0.5 hrs to about 1.5 hrs at room temperature. The reaction is advantageously effected at a temperature ranging from room temperature to the boiling point of the solvent to be used for from about 1 hr to about 3 hrs. In the above reaction, from about 0.5 mol to about 1.5 mol, preferably from about 0.8 mol, to about 1 mol of phosphorus a oxyhalide is conveniently employed per 1 mol of halogenated dihydroxy compound.

The equation of the reaction is as follows:

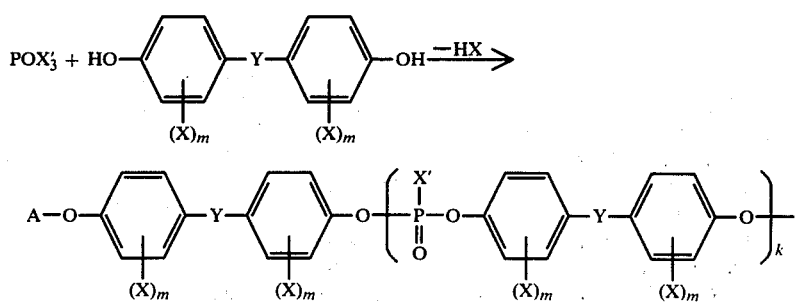

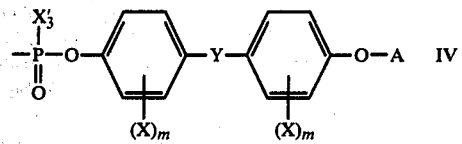

wherein Y, X and x' are as defined above, A is H or

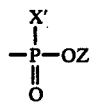

wherein Z is H or a residue of the terminator and k is integer of from 0 to 8.

In the product represented by the above equation, whether A is H or

depends on the molar ratio of the reactants, the reaction conditions, and the like.

The residues of terminators represented by Z in the formula

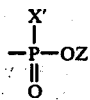

include, for example residues of phenol, alkylphenol, halo-nucleus-substituted phenol, halo-nucleus-substituted alkylphenol, aniline, and halo-nucleus-substituted aniline.

All of the compounds represented by formula IV are usable as flame retardants for synthetic resins of the present invention.

In general, in the formula IV, the compounds wherein A is

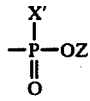

are insoluble in the reaction solvent, such as methylene chloride. So, the resulting product is formed as a precipitate after completing the reaction. In the formula IV, the compounds of lower molecular weight wherein A is H are soluble in methylene chloride.

In formula I, the compounds wherein l is more than 10 have poor compatibility with the synthetic resins which will constitute a matrix in a mixture of the resin and such a compound. As a result, when such compound is incorporated in the resin, it bleeds on the surface of the molded product, whereby the appearance of the molded product is noticeably impaired.

The phosphorus-oxyhalides employed in the preparation of the flame retardant of the present invention include, for example, phosphorus oxytrichloride, phosphorus-oxytribromide, and the like.

The halogenated dihydroxy compounds having the formula

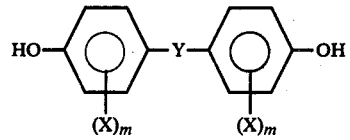

employed in such preparation include, for example, bis(4-hydroxy-2-bromophenyl)methane, bis(4-hydroxy-3-bromophenyl)methane, bis(4-hydroxy-3-chlorophenyl)methane, bis(4-hydroxy-3,5-dibromophenyl)methane, bis(4-hydroxy-3,5-dichlorophenyl)methane, 1,1-bis(4-hydroxy-3-chlorophenyl)ethane, 1,1-bis(4-hydroxy-3-bromophenyl)ethane, 1,1-bis(4-hydroxy-3,5-dichlorophenyl)ethane, 1,1-bis(4-hydroxy-3,5-dibromophenyl)ethane, 1,2-bis(4-hydroxy-3-chlorophenyl)ethane, 1,2-bis(4-hydroxy-3-bromophenyl)ethane, 1,2-bis(4-hydroxy-3,5-dichlorophenyl)ethane, 1,2-bis(4-hydroxy-3,5-dibromophenyl)ethane, 2,2-bis(4-hydroxy-2-bromophenyl)propane, 2,2-bis(4-hydroxy-3-chlorophenyl)propane, 2,2-bis(4-hydroxy-3-bromophenyl)propane, 2,2-bis(4-hydroxy-3,5-dibromophenyl)propane, 2,2-bis(4-hydroxy-3,5-dichlorophenyl)propane, 1,1-bis(4-hydroxy-3,5-dichlorophenyl)butane, 1,1-bis(4-hydroxy-3,5-dichlorophenyl)butane, 1,1-bis(4-hydroxy-3-chlorophenyl)butane, 1,1-bis(4-hydroxy-3-bromophenyl)butane. Of those compounds 2,2-bis(4-hydroxy 3,5-dibromophenyl)propane and 2,2-bis(4-hydroxy-3,5-dichlorophenyl)propane are preferred.

The synthetic resins to which the flame retardant of the present invention is added for imparting flame retardancy to the resin include for example, thermoplastic resins, that is, a homopolymer such as polyethylene, polypropylene, polystyrene; a copolymer, such as styrenebutadiene copolymer; styrene-butadiene-acrylonitrile terpolymer (including ABS resin); blending polymer consisting of homopolymer thereof, homopolymer of styrene, butadiene or acrylonitrile, and/or copolymer thereof; polyester; polycarbonate; polyamide; polyacetal; polyurethane and mixture thereof; and a thermosetting resin, such as a phenol resin and an epoxy resin.

When a resin incorporating the flame retardant of the present invention is burnt, the drippings of the resin do not fall. So, the flame retardant of the present invention imparts excellent flame retardancy to the resins, when incorporated therein.

The flame retardant of the present invention may be incorporated in the synthetic resin alone. Or it may be used in conjunction with a flame retardant promotor, such as antimony trioxide, bismuth trioxide, tin oxide, zirconium oxide and the like.

Any conventional process may be used for incorporating the flame retardant of the present invention in the synthetic resin including, for example, the dry blend method comprising mixing the retardant with resin pellets; the wet blend method comprising mixing a solution of the retardant in a solvent with molten resin; the immersion method comprising immersing the molded product in a solution of the retardant in a solvent; and the coating method comprising coating the solution of the retardant on the molded product.

The amount of the flame retardant employed is not critical. The amount depends on whether the flame retardant promoter is used or not, the degree of flame retardancy desired and the like. More than 5% by weight, preferably from about 10 to about 20% by weight of the flame retardant is conveniently employed on the basis of total weight of the resin and the flame retardant.

Knonw heat stabilizers, light stabilizers, colorants, inorganic fillers, and/or lubricants may be added to the flame retardant-incorporating resin.

Tests on the flame retardancy effectiveness of the present invention were carried out in accordance with UL Standard.

The term "UL" means Underwriters Laboratories Inc. in the United States. The Underwriters Laboratories Inc. is a public safety organization. The Underwriter Laboratories Inc. describes the test for flammability of a plastic. The standard of the test is UL 94. In UL 94 Test Standard there are 4 classes, 94 V-0, 94 V-1, 94 V-2, 94 HB for evaluating the degree of flame retardancy.

This invention is further illustrated, but in no way limited, by the following Examples. The parts and percent by weight unless otherwise specified.

EXAMPLE 1

Preparation of flame retardant of this invention.

In a four necked flask equipped with agitator, cooler, thermometer and dropping funnel was charged 0.3 mol of sodium salt of tetrabromo bisphenol A namely, 2,2-bis(4-hydroxy-3,5-bromophenyl)propane. To the flask was added 200 ml of dry methylene chloride to prepare a suspension of tetrabromobisphenol A. A solution of 0.2 mol of phosphorus oxytrichloride in 100 ml of dry methylene chloride was added dropwise to the suspension from the dropping funnel over 1 hour at room temperature. After the dropping step is completed, the mixture was gradually heated to 40° C. over 1 hour with stirring. Then 1.0 ml of triethylamine was added to the mixture. The agitation of the solution was continued for 5 hours to complete the reaction. After the reaction was completed, precipitate (referred to as product B) was separated from methylene chloride phase dissolving product A through filtration. Product was ground and was boiled in boiling water for 1 to 2 hrs., and was washed with methanol to obtain 120 g of white solid material having melting point of from 225° to 228° C. (referred to as product B'). Product B' was insoluble in methanol or dioxane, was wettable with methylene or tetrahydrofuran and was soluble in dimethyl acetamide. The content of phosphorus in product B' was 6.2%; and the content of Cl in P-Cl type in product B' was 5.0%. Product B' was confirmed through infrared absorption analysis to be the reaction product of tetrabromophenol A with phosphorus oxytrichloride.

The product B' was washed with boiling water. The content of phosphorus in treated product B' was 3.3%; and the content of Cl in P-Cl type therein was 4.5%. The treated product B' was insoluble in methanol or dioxane, was wettable with methylene chloride or tetrahydrofuran and was soluble in dimethyl acetamide. Product B' had an intrinsic viscosity of 0.027 when a solution of product B' in dimethyl acetamide was measured. This intrinsic viscosity value corresponds to a polymerization degree of 4.

The filtrate (methylene chloride phase containing product A) was poured into a large amount of methanol to obtain 30 g of white solid material (product A') having melting point of 176° to 178° C. Product A' was confirmed to be the reaction product of tetrabromobisphenol A with phosphorus oxyrichloride. Molecular weight, content of phosphorus and content of Cl in P-Cl type of product A' were measured.

The results are shown in the following.

|  | Molecular weight | Content of P (%) | Content of Cl in P-Cl type (%) |
|---|---|---|---|
| Measured | 1156 | 2.9 | 3.7 |
| Theoretical | 1167.5 | 2.6 | 3.1 |

We found from the results that product A' was a compound having the formula

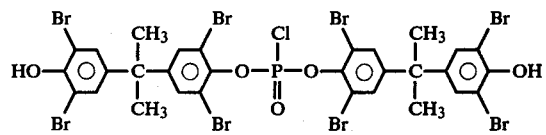

EXAMPLE 2

In a four necked flask equipped with agitator, cooler, thermometer and dropping funnel was charged 0.3 mol of tetrabromobisphenol A. 100 Ml of dry methylene chloride and 100 ml of pyridine were added to the mixture, and 1 mol of NaOH was added thereto. A solution of 0.2 mol of phosphorus oxytrichloride in 100 ml of dry methylene chloride was added dropwise to the resulting mixture from the dropping funnel over 1 hour at room temperature. After the dropping step was completed, the mixture was gradually heated to 40° C. over 1 hour with stirring. The reaction was continued for an additional 4 hrs. After the reaction was completed, the solvent and pyridine were separated from the reaction product by a conventional method and treated in the same way as in Example 1 to obtain white solid material. The intrinsic viscosity of the solid was 0.047 when a solution of the solid in dimethyl acetamide was measured. This intrinsic viscosity value corresponds to a polymerizaton degree of 8.

We found that the solid material is the same as product B' in Example 1.

EXAMPLE 3

The procedure of Example 1 was repeated except that tetrachlorobisphenol A, namely 2,2-bis(4-hydroxy-3,5-dichlorophenyl)propane was used. As in Example 1, a white solid having melting point of from 225° to 230° C. was obtained. The intrinsic viscosity of the solid was 0.033 when a solution of the solid in dimethyl acetamide was measured.

EXAMPLE 4

Preparation of flame retardant in case POX$_3$ is POBr$_3$.

In a four necked flask equipped with agitator, cooler, thermometer and dropping funnel was charged 0.3 mol of tetrabromobisphenol A. 200 Ml of dry methylene chloride, 1.0 mol of triethylamine as a catalyst and 0.75 mol of sodium hydroxide were added to the tetrabromobisphenol A to produce a suspension. A solution of 0.2 mol of phosphorus oxytribromide in 100 ml of dry methylene chloride was added dropwise to the suspension from the dropping funnel over 1 hour at room temperature. After the dropping step is completed, 300 ml of water was added to the mixture. Agitation of the mixture was continued for an addtional 2 hrs. to obtain 115 gr. of white solid precipitate. The precipitate was insoluble in methanol or dioxane, was somewhat wettable with methylene chloride or tetrahydrofuran and was soluble in dimethyl acetamide. The precipitate was purified and ground in the same way as in Example 1 to obtain white solid product having melting point of from 225° to 230° C. The product was confirmed through infrared absorption analysis to be the reaction product of tetrabromobisphenol A with phosphorus oxytribromide. Measured intrinsic viscosity of the solid was 0.040 (as dimethylacetamide solution).

EXAMPLES 5–11

Product B' prepared in Example 1 was added to each of the resins as shown in Table 1. Article ⅛ inch thick, 0.5 inch wide and 5 inches long was obtained by molding each of the resins incorporating product B'. The flaming-test of the molded articles was conducted in accordance with UL 94 Standard. The results are shown in Table 1.

For comparison, the flame retardant of the prior art was added to each of the resins as shown in Table 1. The molding step and the combustion test were conducted in the above way. The results are shown in Table 1 as control tests 1 and 2.

Table 1

| Example No. | Amount of flame retardant added (%) | Amount of Sb$_2$O$_3$ added | Resins employed | UL 94 flame class | Drippings of resin |
|---|---|---|---|---|---|
| 5 | 20 | 0 | polystyrene | 94 V-0 | Non |
| 6 | 15 | 5 | polystyrene | 94 V-0 | Non |
| 7 | 20 | 0 | High-impact polystyrene | 94 V-0 | Non |
| 8 | 15 | 5 | High-impact polystyrene | 94 V-0 | Non |
| 9 | 20 | 0 | ABS | 94 V-0 | Non |
| 10 | 15 | 5 | ABS | 94 V-0 | Non |
| 11 | 10 | 0 | poly-carbonate | 94 V-1 | ++ |
| Control 1 | 20* | 5 | High-impact polystyrene | 94 V-2 | + |
| Control 2 | 20** | 5 | polystyrene | 94 V-2 | + |

+: Dripping that ignited the cotton
++: Dripping, but did not ignited the cotton
*: Flame retardant of prior art employed in control 1 is the compound having the formula

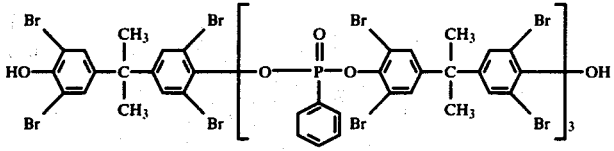

**: Flame retardant of prior art employed in control is the compound having the formula

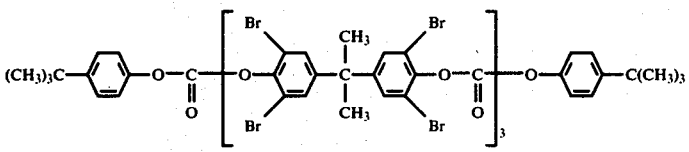

EXAMPLE 12–15

The procedure of Examples 5–11 were repeated except that product A' was employed in place of product B'. The results are shown in Table 2.

Table 2

| No. | Amount of flame retardant added (%) | Amount of Sb$_2$O$_3$ added | Resins employed | UL flame class | Drippings of resin |
|---|---|---|---|---|---|
| 12 | 20 | 0 | polystyrene | 94 V-0 | Non |
| 13 | 20 | 0 | High-impact polystyrene | 94 V-0 | Non |
| 14 | 20 | 5 | ABS | 94 V-0 | Non |
| 15 | 10 | 0 | poly-carbonate | 94 V-1 | ** |

** Dripping, but did not ignite the cotton

EXAMPLE 16

(a) The product obtained in Example 3 in the amount of 20% by weight or (b) said product in the amount of 15% by weight and antimony trioxide in the amount of 5% by weight was incorporated in high-impact polystyrene. The molding step and the combustion test were effected in the same way as in Example 4. The class of all flame retardancy were UL 94 V-0.

What we claim is:

1. A flame retardant for synthetic resins comprising an oligomer having the following structural formula:

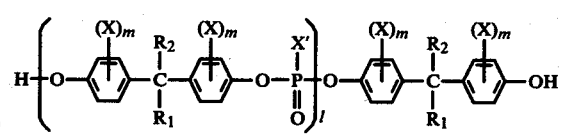

wherein $R_1$ and $R_2$ are independently H or an alkyl of $C_1$–$C_3$, X and X' are independently Br or Cl, m is 1 or 2 and l is an integer of from 1 to 10.

2. The flame retardant of claim 1 wherein l is from 2 to 10.

3. The flame retardant of claim 1, wherein l is 1.

4. The flame retardant of claim 1, wherein x is Cl or Br and X' is Cl.

5. The flame retardant of claim 1, wherein X and X' are Cl.

6. A flame retardant for synthetic resins according to claim 1 wherein Y is

7. A flame retardant for synthetic resins according to claim 1 wherein Y is

X is Cl or Br, and X' is Cl.

8. A flame retardant of claim 1 wherein the oligomer is a reaction product of a phosphorus oxyhalide having the formula $$POX'_3$$

wherein X' is Cl or Br, with a halogenated dihydroxy compound having the formula

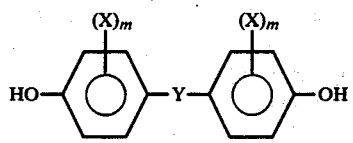

wherein Y is

wherein $R_1$ and $R_2$ are independently H or an alkyl of $C_1$–$C_3$, X is Br or Cl, and m is 1 or 2.

9. The flame retardant according to claim 8 wherein the phosphorus oxyhalide is phosphorus oxytrichloride.

10. The flame retardant according to claim 8 wherein the halogenated dihydroxy compound is 2,2-bis(4-hydroxy-3,5-dibromophenyl) propane.

* * * * *